(12) United States Patent
Kroll et al.

(10) Patent No.: US 7,139,611 B1
(45) Date of Patent: Nov. 21, 2006

(54) SYSTEM AND METHOD FOR REJECTING FAR-FIELD SIGNALS USING AN IMPLANTABLE CARDIAC STIMULATION DEVICE

(75) Inventors: Mark W. Kroll, Simi Valley, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 497 days.

(21) Appl. No.: 10/430,039

(22) Filed: May 5, 2003

(51) Int. Cl.
*A61N 1/05* (2006.01)
(52) U.S. Cl. ...................................... 607/28
(58) Field of Classification Search ............. 607/4, 607/5, 9, 17, 18, 25; 600/509; 128/901
See application file for complete search history.

(56) References Cited

U.S. PATENT DOCUMENTS

| | | | |
|---|---|---|---|
| 5,275,621 A | 1/1994 | Mehra | 607/5 |
| 5,755,739 A | 5/1998 | Sun et al. | 607/14 |
| 5,759,196 A | 6/1998 | Hess et al. | 607/14 |
| 5,776,168 A * | 7/1998 | Gunderson | 607/27 |
| 6,516,225 B1 | 2/2003 | Florio | 607/9 |
| 6,539,259 B1 * | 3/2003 | Weinberg et al. | 607/9 |

* cited by examiner

*Primary Examiner*—Jeffrey R. Jastrzab
*Assistant Examiner*—Darin Roberts

(57) ABSTRACT

A technique is provided for filtering far-field electrical cardiac signals from near-field signals. Atrial tip and ring signals are sensed using unipolar electrodes and any timing differences between corresponding events within the signals are detected. Then, far-field signals are filtered from the tip and ring signals based on the detected timing differences, such that substantially only near-field atrial signals remain. The technique exploits the fact that near-field atrial signals are sensed when a conduction wave passes by the atrial electrodes. In contrast, far-field signals from the ventricles propagate to the atrium at near the speed of light. Hence, any significant timing difference between corresponding events appearing in the atrial signals is indicative of a near-field event, whereas the lack of a significant timing difference is indicative of a far-field event. In one example, a sense amplifier is provided with a Boolean logic circuit to aid in time delay-based filtering.

12 Claims, 9 Drawing Sheets

SYSTEM AND METHOD FOR REJECTING FAR-FIELD SIGNALS USING AN IMPLANTABLE CARDIAC STIMULATION DEVICE

FIELD OF THE INVENTION

The invention generally relates to implantable cardiac stimulation devices such as pacemakers and implantable cardioverter/defibrillators (ICDs) and, in particular, to techniques for rejecting far-field ventricular signals from cardiac signals sensed in the atria.

BACKGROUND OF THE INVENTION

Many pacemakers and ICDs include one or more leads mounted in the atria for directly sensing atrial events, particularly P-waves. Reliable P-wave detection is required so as to determine the atrial rate for detecting atrial fibrillation and for controlling atrial pacing functions, such as dynamic atrial overdrive (DAO) pacing. A long-standing problem with atrial sensing is that electrical signals generated in the ventricles often appear within the atrial signals and can be misinterpreted as P-waves. The signals from the ventricles are referred to as far-field signals. Indeed, because the ventricles are considerably more massive than the atria, depolarization of ventricles generates R-waves having magnitudes far greater than P-waves. Even when sensed with leads mounted within the atria, the far-field R-waves often appear with at least the same magnitude as the near-field P-waves, making it quite difficult to reliably detect only P-waves. Note that, strictly speaking, P-waves and R-waves are features of a surface electrocardiogram (EKG). For convenience, herein, the terms P-wave and R-wave are also used to refer to the corresponding internal electrical signal component.

The far-field sensing problem is illustrated in FIG. 1, which shows a atrial bipolar tip-ring signal 1 derived from atrial tip and ring electrodes, along with a corresponding surface EKG cardiac signal 2. As can be seen, within the atrial signal, P-wave 3 is well represented. However, R-wave 4 also appears within the atrial signal, with about the same magnitude as the P-wave. Accordingly, detection circuitry designed to detect events within the atrial signal may have trouble distinguishing between the P-waves and R-waves and, in particular, may count both events as P-waves for the purposes of atrial rate calculation, likely resulting in the calculated atrial rate being twice the actual atrial rate. For ICDs configured to deliver a high energy cardioversion shock to terminate atrial fibrillation, the erroneous calculation of the atrial rate may result in a painful cardioversion shock being delivered even though none is actually required.

FIG. 2 illustrates a typical atrial sense amplifier used for sensing atrial signals. An algebraic difference between input tip and ring atrial signals is generated by differential amplifier 5, yielding the bipolar tip-ring signal (signal 1 of FIG. 1.) The bipolar tip-ring signal is smoothed by filter 6 then rectified by rectifier 7 before being routed into comparator 8, which also receives a sense threshold voltage along line 9. The comparator outputs a sense pulse signal indicative of whether the rectified bipolar tip-ring signal exceeds the threshold voltage. The analog bipolar tip-ring signal is also output for separate processing by other components. When using the circuit of FIG. 2 to process atrial signals, such as those shown in FIG. 1, both the near-field P-wave and the far-field R-wave trigger a sense pulse due to their significant voltage swings, resulting in erroneous detection of the atrial rate, erroneous overdrive rate adjustments, and possible delivery of an unnecessary cardioversion shock.

Accordingly, it would be highly desirable to provide a technique for properly rejecting far-field events from atrial signals and in particular for providing an improved atrial sense amplifier capable of far-field rejection for use in a pacemaker or ICD. It is to these ends that the invention is primarily directed.

Summary

In accordance with the invention, a technique is provided for use with an implantable cardiac stimulation device for filtering far-field signals sensed by a pair of electrodes mounted in the heart. Cardiac electrical events are independently sensed using the two electrodes and timing differences, if any, are detected. Then far-field signals are filtered from the sensed signals using the detected timing difference such that substantially only near-field atrial signals remain.

In an exemplary embodiment, the pair of electrodes are tip and ring electrodes mounted within the atria and the technique is performed to filter far-field signals arising from the ventricles from atrial signals so as to allow for reliable detection of P-waves while properly rejecting R-waves. The invention exploits the fact that near-field signals are sensed when a conduction wave passes by the atrial sensing electrodes. In contrast, far-field signals from the ventricles propagate to the atrium at near the speed of light. Hence, any significant timing difference between corresponding events appearing in the atrial signals is indicative of a near-field event, whereas the lack of a significant timing difference is indicative of a far-field event.

In the exemplary embodiment, a sense amplifier is provided with a Boolean logic circuit to aid in time delay-based filtering. Timing differences between events in the tip and ring signals are detected by routing Boolean versions of the tip and ring signals through the logic circuit, which is operative to generate a difference signal identifying portions of the atrial tip and ring signals subject to near-field time-delays. In one specific example, the logic circuit includes an AND-gate with a single inverted input. In another example, the logic circuit includes an exclusive-OR-gate (XOR-gate.) In either case, the resulting difference signal, which is also a Boolean signal, is then bandpass filtered to yield an analog signal for combination with an analog bipolar tip-ring signal to yield a near-field signal representative of near-field events sensed by the pair of electrodes. The near-field signal is compared against a sense threshold to detect atrial events.

Thus, improved techniques are provided for filtering far-field signals from electrical cardiac signals so as to allow for reliable detection of near-field events. Other features, objects and advantages of the invention are set forth below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
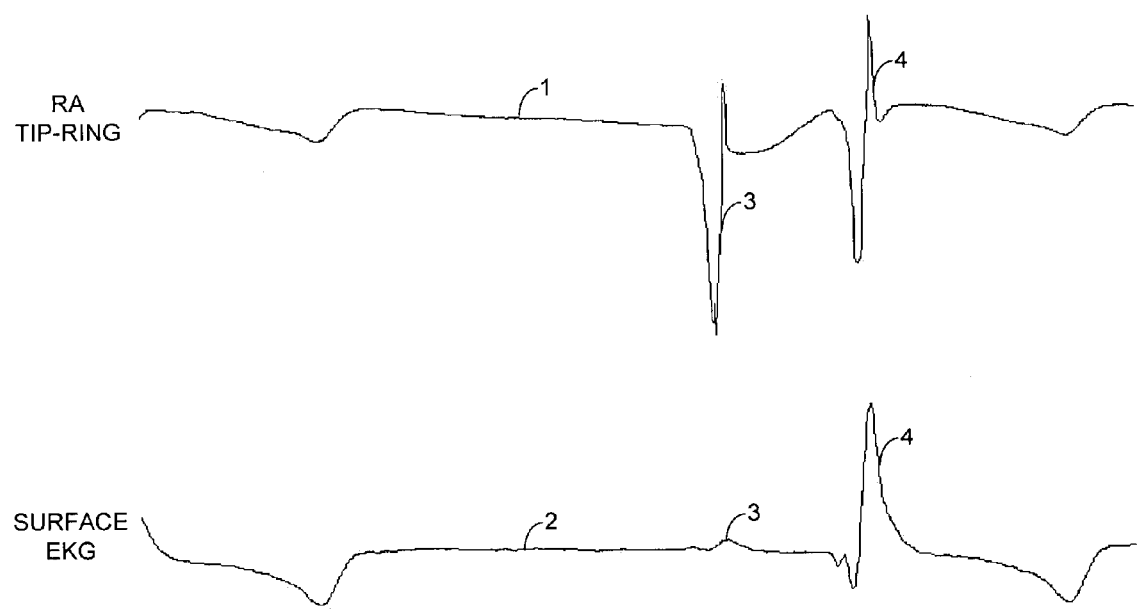
FIG. 1 is a graph illustrating the effects of far-field sensing on exemplary electrical cardiac signals derived internally using RA tip and ring electrodes, along with a corresponding surface EKG.
Figure 2:
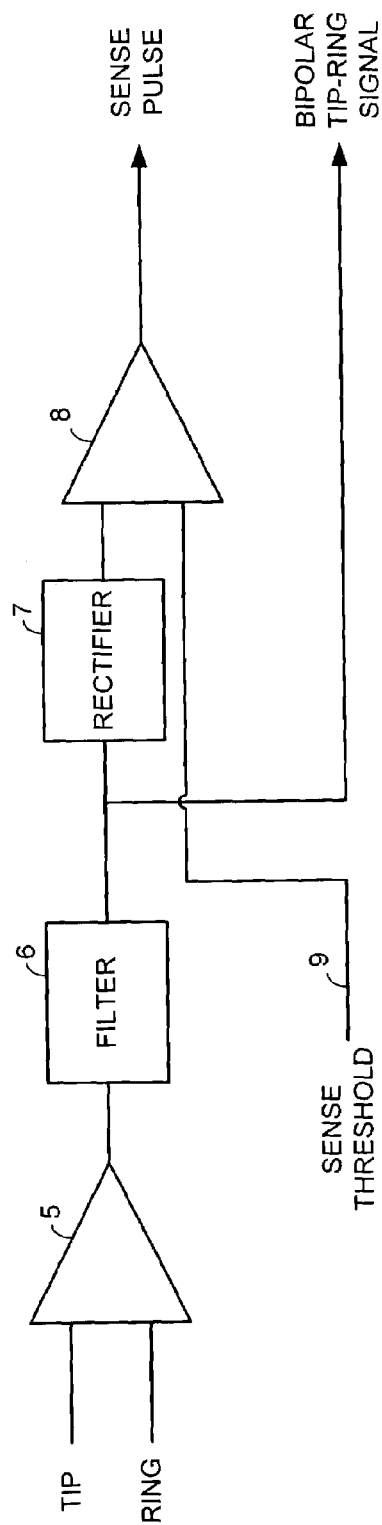
FIG. 2 is a functional block diagram illustrating components of a sense amplifier configured in accordance with the prior art for detecting atrial events within the internal electrical cardiac signals such as shown in FIG. 1.
Figure 3:
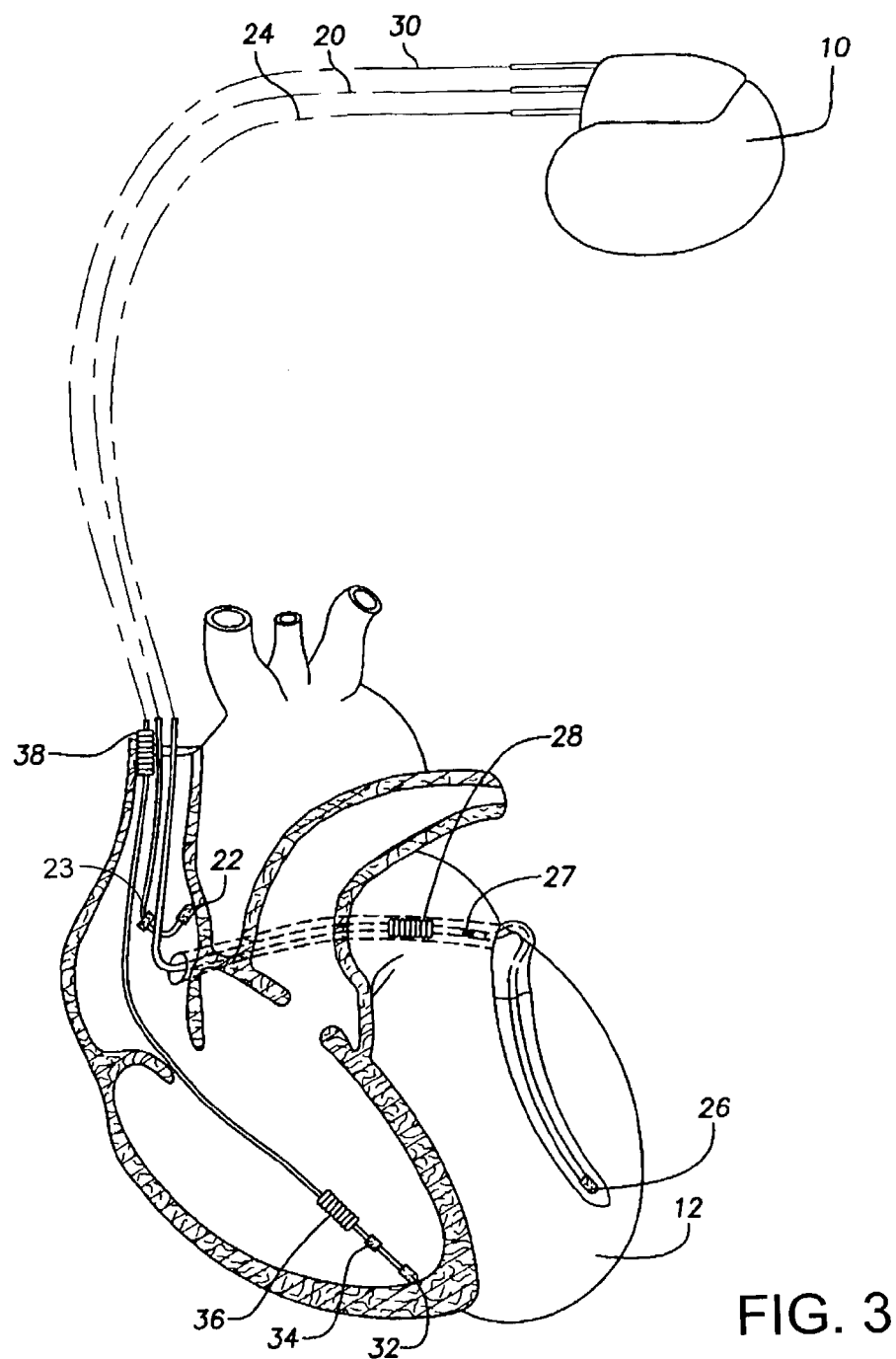
FIG. 3 is a simplified diagram illustrating an implantable stimulation device in electrical communication with at least three leads implanted into the heart of a patient for delivering multi-chamber stimulation and shock therapy including cardioversion therapy and overdrive pacing therapy.

As shown in FIG. 3, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 4:
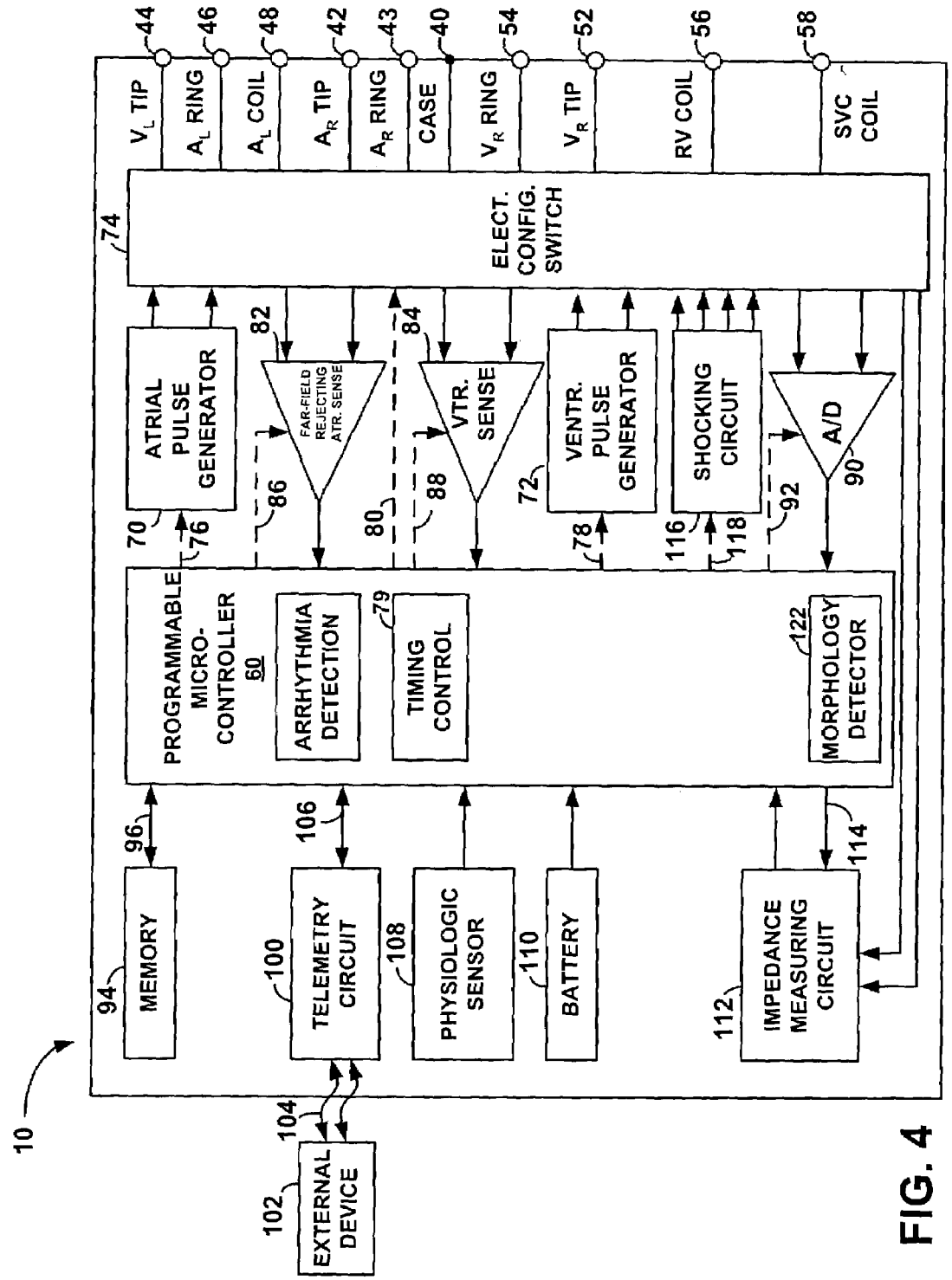
FIG. 4 is a functional block diagram of the implantable cardiac stimulation device of FIG. 3 illustrating basic elements of the stimulation device including an improved atrial sense amplifier capable of rejecting far-field signals to yield filtered near-field signals.

As illustrated in FIG. 4, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 4, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 are selectively coupled to the right atrial lead 20, coronary sinus lead 24, and the right ventricular lead 30, through the switch 74 for detecting the presence of cardiac activity in each of the four chambers of the heart. As will be explained below, atrial sensing circuit 82 is a far-field rejecting circuit configured to reject far-field signals arising from the ventricles while retaining near-field signals from the atria.

The atrial and ventricular sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries. As further shown in FIG. 4, the device 10 is shown as having an impedance measuring circuit 112 which is enabled by microcontroller 60 via a control signal 114.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Overview of Atrial Sense Amplifier

Figure 5:
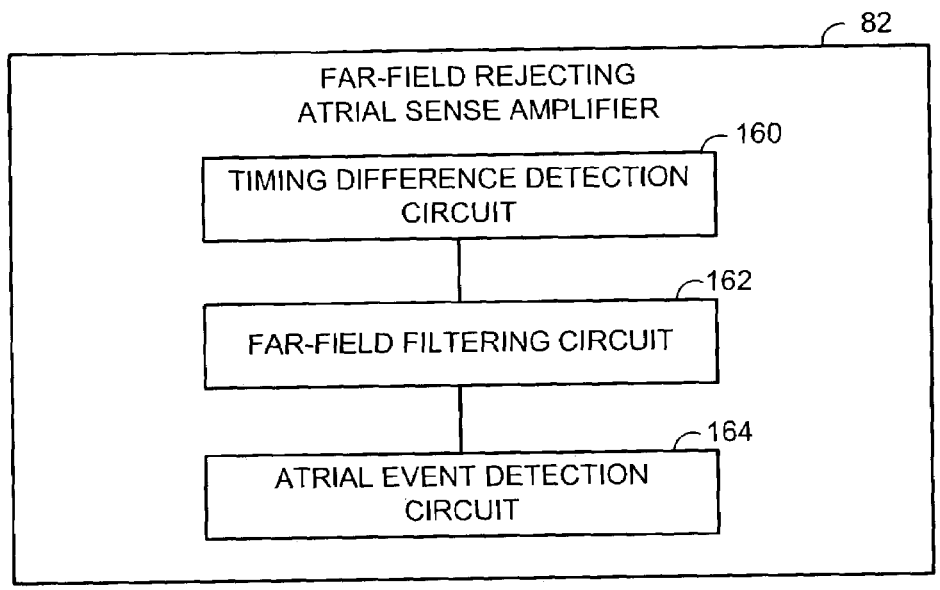
FIG. 5 is a block diagram of pertinent components of the atrial sense amplifier of FIG. 4.
Figure 6:
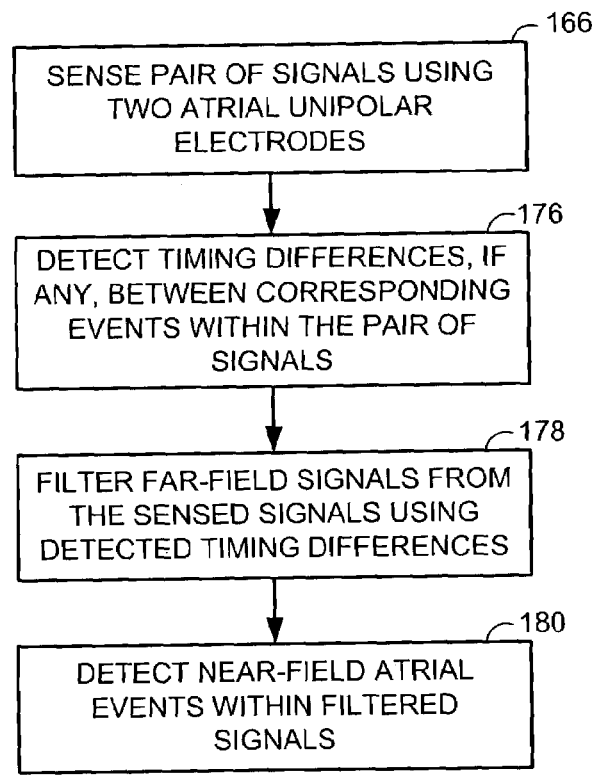
FIG. 6 is a flow chart illustrating, at a high level, steps performed by the atrial sense amplifier of FIG. 5.
Figure 7:
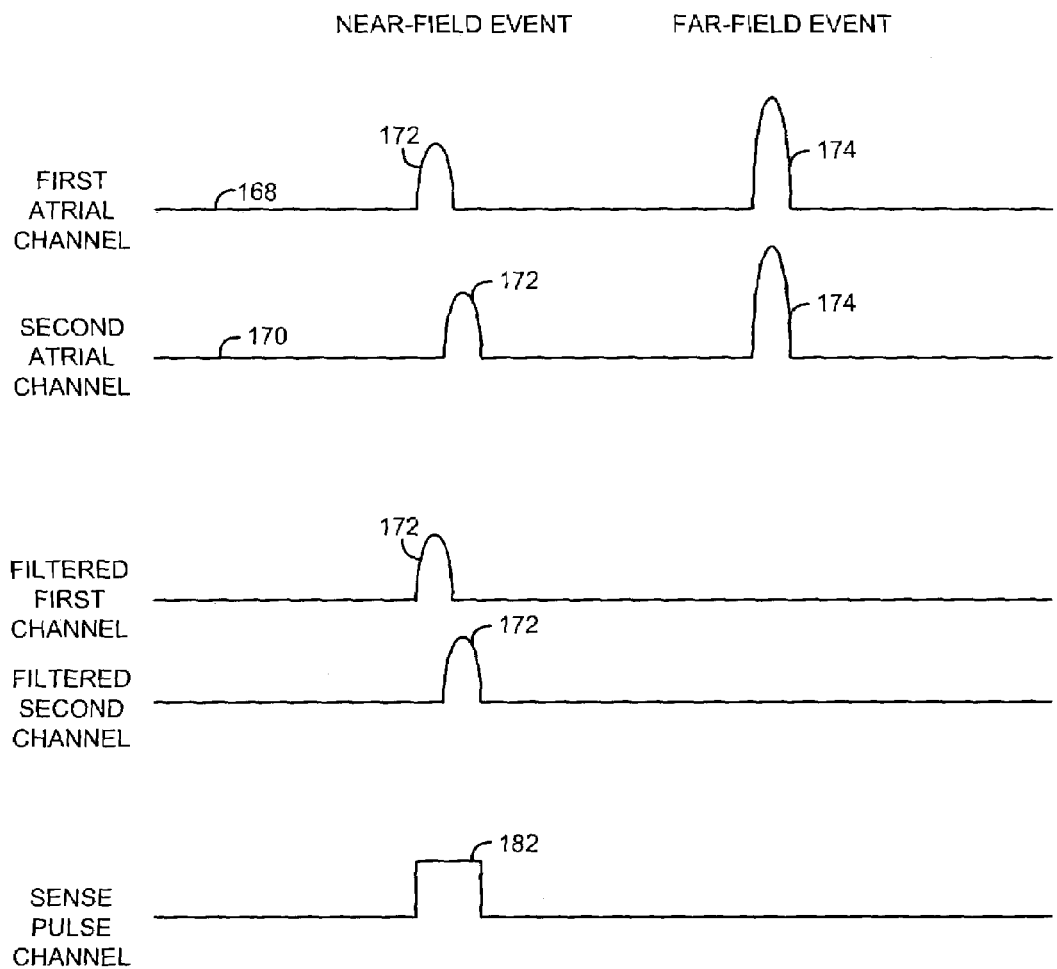
FIG. 7 is a graph illustrating exemplary, stylized atrial signals processed by the atrial sense amplifier of FIG. 5 and in particular illustrating the time delay occurring within near-field signals.

Referring to FIGS. 5–7, an overview of far-field rejecting atrial sense amplifier 82 of FIG. 4 will now be provided. Far-field signals arising from the ventricles (i.e. R-waves) propagate much faster through the atria than near-field signals arising from the atria (i.e. P-waves) and hence a pair of unipolar electrodes mounted within the atria sense corresponding far-field events simultaneously but sense near field events subject to a slight time-delay. Near-field signals are sensed when a conduction wave passes by the atrial sensing electrodes. In contrast, far-field signals from the ventricles propagate through the atrium at near the speed of light. More specifically, a near-field voltage difference is generated in the atria by an atrial depolarization wave traveling through the atrial tissue past two atrial electrodes. The depolarization wave moves at about 100–400 cm/s. The far-field signal is generated in a similar manner (traveling wave of depolarization in the ventricles) but the ventricular depolarization wave never travels past the atrial electrodes. However, voltage differences generated across the ventricles by ventricular depolarization are large enough to also be sensed in the atrium (and, to varying degrees, everywhere in the thorax) through the global voltage divider formed by the conductive tissues and fluids in the body. The far-field voltage differences propagate near the speed of light. Hence, near-field atrial signals exhibit a conduction delay between electrodes whereas far-field ventricular signals do not exhibit any significant conduction delay. The sense amplifier of FIG. 5 is configured to reject events sensed simultaneously by the pair of unipolar atrial electrodes while retaining events that are subject to a time delay indicative of near-field propagation delays. To this end, the sense amplifier includes three main components: a timing difference detection circuit 160, a far-field filtering unit 162, and an atrial event detection unit 164.

Briefly, with reference to FIG. 6, the atrial sense amplifier, at step 166, receives a pair of signals sensed within the atria using a pair of atrial unipolar electrodes (such as atrial tip and ring electrodes 22 and 23 of FIG. 3.) Exemplary atrial channel signals 168 and 170 are shown in FIG. 7. Each includes a near-field event 172 (i.e. a P-wave) and a far-field event 174 (i.e. an R-wave). Note that the signals shown in FIG. 7 are merely stylized representations of atrial channel signals provided to help clearly illustrate the principles of the invention and should not be construed as representations of actual cardiac signals sensed within the atria. In any case, at step 176 of FIG. 6, the timing difference detection circuit detects timing differences, if any, between corresponding events within the pair of atrial channel signals, i.e. the sense amplifier detects the timing difference between event 172 as it appears within the pair of atrial channel signals. At step 178, the far-field filtering circuit of the sense amplifier filters far-field signals from the atrial channel signals using the detected timing differences. More specifically, events that occur simultaneously within the pair of atrial channel signals are eliminated whereas events subject to a slight time delay are retained. In an alternative embodiment, events that occur within a few milliseconds within the pair of atrial channels are considered sufficiently simultaneous and are therefore eliminated as being far-field events, while events subject to a slight time delay (e.g., more than a few milliseconds in the one illustrative embodiment) are identified as near-field signals.

The resulting filtered atrial channel signals are also shown in FIG. 7. As can be seen, the far-field events being substantially simultaneous are completely eliminated; whereas the near-field events, having the slight time delay, are retained. Finally, at step 180, the sense amplifier detects events remaining within the filtered signals and generates a corresponding sense pulse 182 indicative of a P-wave. In the example of FIG. 7, both the first and second atrial channels are separately filtered to eliminate far-field events. This is not required. In the circuit implementations described below, separate atrial tip and ring signals are first merged into a single bipolar signal, which is then filtered to eliminate far-field events. The sense pulse is generated based upon events detected within the filtered bipolar signal.

Specific Circuit Implementations of Atrial Sense Amplifier

With reference to the remaining figures, exemplary circuit implementations of the sense amplifier of FIG. 5 will be described. In a first implementation, shown in FIG. 8, a Boolean logic circuit having an AND-gate with an inverted input on a ring channel is employed for identifying portions of the atrial signals having timing differences associated with near-field events. Timing diagrams of exemplary signals are set forth in FIG. 9. Briefly, rectified versions of input tip and ring signals 200 and 202 are compared against respective thresholds to generate separate Boolean tip and ring signals 204 and 206. The thresholds are shown using dashed lines. (The intermediate rectified versions of the signals are not separately shown.) The resulting Boolean tip and ring signals are combined using the AND-gate to output a Boolean difference signal 208. The difference signal is HIGH (or set to "1") whenever the Boolean tip signal is HIGH and the Boolean ring signal is LOW. The difference signal is LOW (or set to "0") at all other times. In this manner, difference signal 208 identifies time periods when the rectified tip signal is large but the rectified ring signal is small due to the presence of an event subject to a near-field propagation time delay, such as exemplary P-wave 210.

Figure 9:
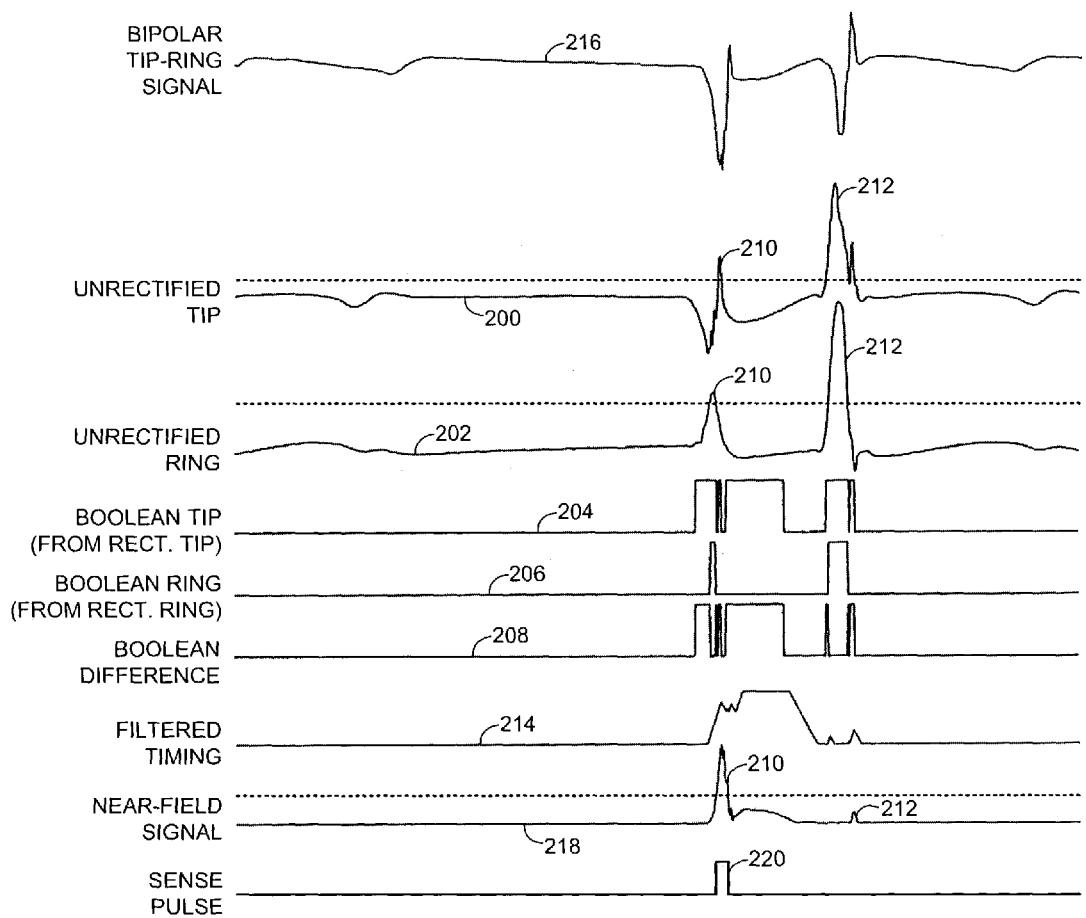
FIG. 9 is a graph illustrating exemplary electrical cardiac signals derived internally using right atrial tip and ring electrodes along with resulting filtered near-field signals generated using the atrial sense amplifier of FIG. 8.

In the specific example of FIG. 9, the initial signal deflection indicative of the onset of the P-wave occurs within the tip signal slightly before it occurs within the ring signal. This is due to the cell activation (or depolarization) wave traveling by the tip before it travels by the ring. As a result, the peak of the P-wave (as it appears within the ring signal) occurs during a zero-crossing point of the P-wave (as it appears within the tip signal.) Hence, the corresponding Boolean tip and ring signals are generally out of sync throughout the P-wave, thus generating a HIGH Boolean difference signal throughout most of the P-wave. In contrast, the signal deflections corresponding to an exemplary R-wave 212 occur more or less simultaneously on both the tip and ring channels and so the corresponding Boolean tip and ring signals are generally in sync throughout most the R-wave, thus yielding a LOW Boolean difference signal 208 throughout most of the R-wave. Some overlap may occur between near-field events on the tip and ring channels despite the near-field propagation time delay and so the resulting Boolean difference signal may include short signal drop-offs during the P-wave (see signal 208 of FIG. 9.) Likewise, a slight lack of synchronization may occur within far-field events despite the lack of propagation time delay and so the resulting Boolean difference signal may include some signal spikes during the R-wave (also see signal 208 of FIG. 9.) Accordingly, the Boolean difference signal is filtered to smooth the signal so as to eliminate or reduce any signal spikes, yielding filtered difference signal 214.

The filtered difference signal thus emphasizes near-field events while de-emphasizing far-field events. Simultaneously, the input tip and ring signals are merged to generate an analog bipolar tip-ring signal 216, which is combined with the filtered difference signal to yield an analog near-field signal 218, indicative of only near-field events. As can be seen, the near-field signal includes a strong sharp signal spike corresponding to P-wave 210 but includes only a slight signal deflection corresponding to R-wave 212. The near-field signal is compared again a sense threshold, shown in dashed lines, to generate a sense pulse 220 identifying the P-wave.

Figure 8:
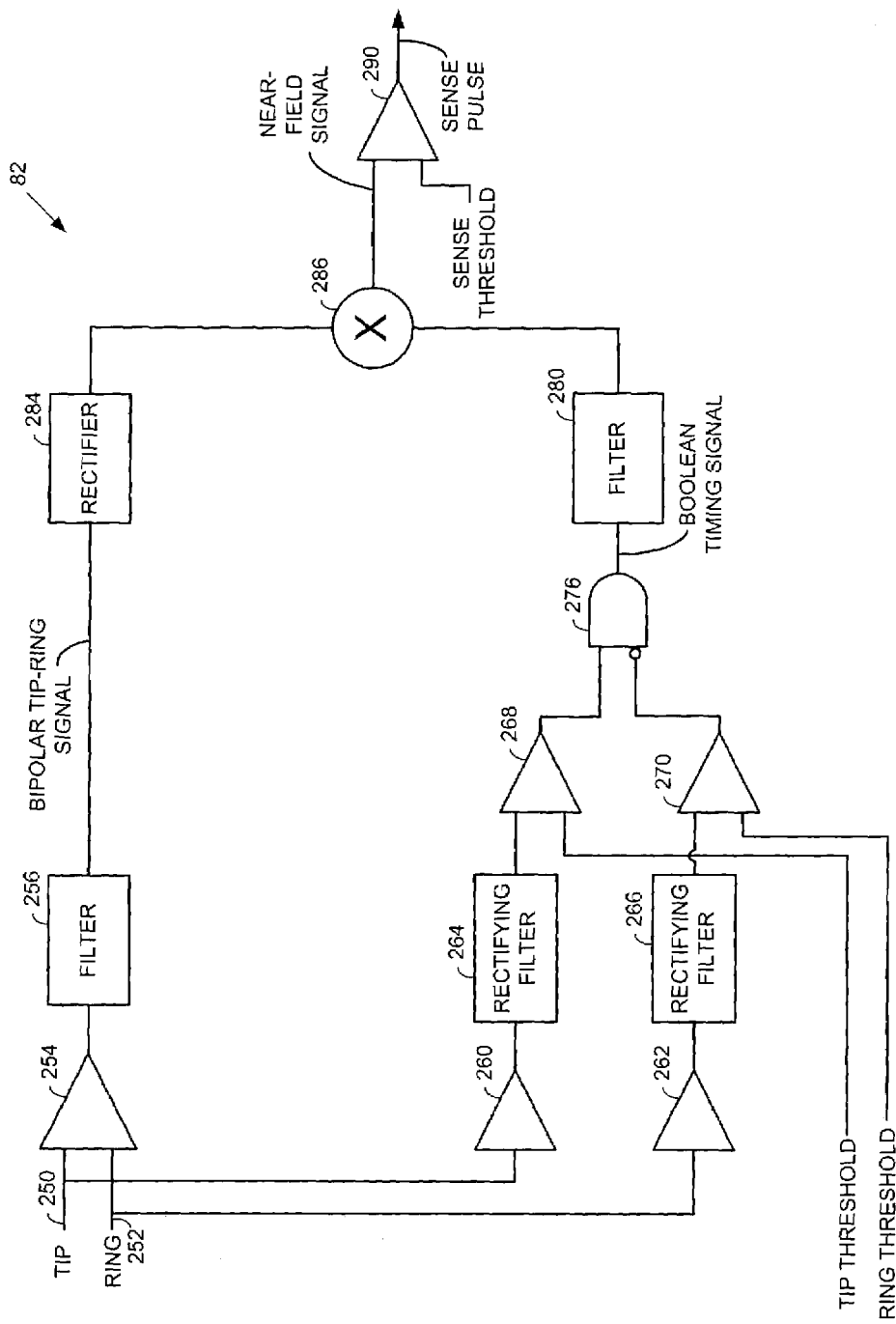
FIG. 8 is a block diagram illustrating components of a first exemplary circuit embodiment of the atrial sense amplifier of FIG. 5, which employs an AND-gate.

Now considering the circuit of FIG. 8 in detail, algebraic differences between input unipolar tip and ring signals received on lines 250 and 252 are amplified by differential amplifier 254 then smoothed by filter 256 to yield analog bipolar tip-ring signal 216 (FIG. 9). The input tip and ring signals are also individually amplified by amplifiers 260 and 262, then smoothed and rectified by rectifying filters 264 and 266. (Although not shown, amplifiers 260 and 262 may also be connected to a unipolar reference signal.) The rectified tip signal is compared against a positive tip threshold voltage using comparator 268 to yield Boolean tip signal 204 (FIG. 9.) Likewise, the rectified ring signal is compared against a positive ring threshold voltage using a comparator 270 to yield Boolean ring signal 206 (also FIG. 9.) The Boolean tip and ring signals are then combined using a Boolean circuit 276, which is an AND-gate having an inverter along the ring input line. As noted, the resulting Boolean difference signal 208 (FIG. 9) is HIGH whenever the Boolean tip signal is HIGH and the Boolean ring signal is LOW. The difference signal is LOW at all other times. The difference signal is then smoothed by filter 280 to yield filtered difference signal 214 (FIG. 9.) Meanwhile, the analog bipolar tip-ring signal is rectified by rectifier 284 and then combined with the filtered difference signal using multiplier 286 to yield analog near-field signal 218 (FIG. 9). The analog near-field signal is compared against a sense threshold voltage via comparator 290 to yield binary sense pulse signal 220 (FIG. 9.) In this manner, the far-field rejecting atrial sense amplifier of FIG. 8 properly rejects far-field R-waves while allowing reliable detection of near-field P-waves.

Thus, the implementation of FIG. 8 employs an AND-gate with a single inverted input to help identify portions of the input atrial signals that incorporate the time-delays associated with near-field signals. The AND-gate is effective, in part, because the tip signal is typically stronger than the ring signal throughout the P-wave. (The tip and ring signals of FIG. 9 are not shown to scale.) Hence, with proper selection of the thresholds for the tip and ring comparators (268 and 270), the Boolean tip signal is HIGH throughout most of the P-wave whereas the Boolean ring signal is LOW and so the resulting difference signal is also HIGH through out most of a P-wave, permitting the P-wave to be retained. The far-field (R-wave) tip and ring signals are typically far stronger than either of the near-field (P-wave) signals and so the Boolean tip and ring signals are HIGH throughout most of the R-wave and the resulting Boolean difference signal is LOW, permitting the R-wave to be filtered out. Appropriate comparator thresholds may be determined via routine experimentation. In implementations where the ring signal is expected to be stronger than the tip signal, the inverter may be instead applied to the tip line with the respective thresholds set accordingly.

Figure 10:
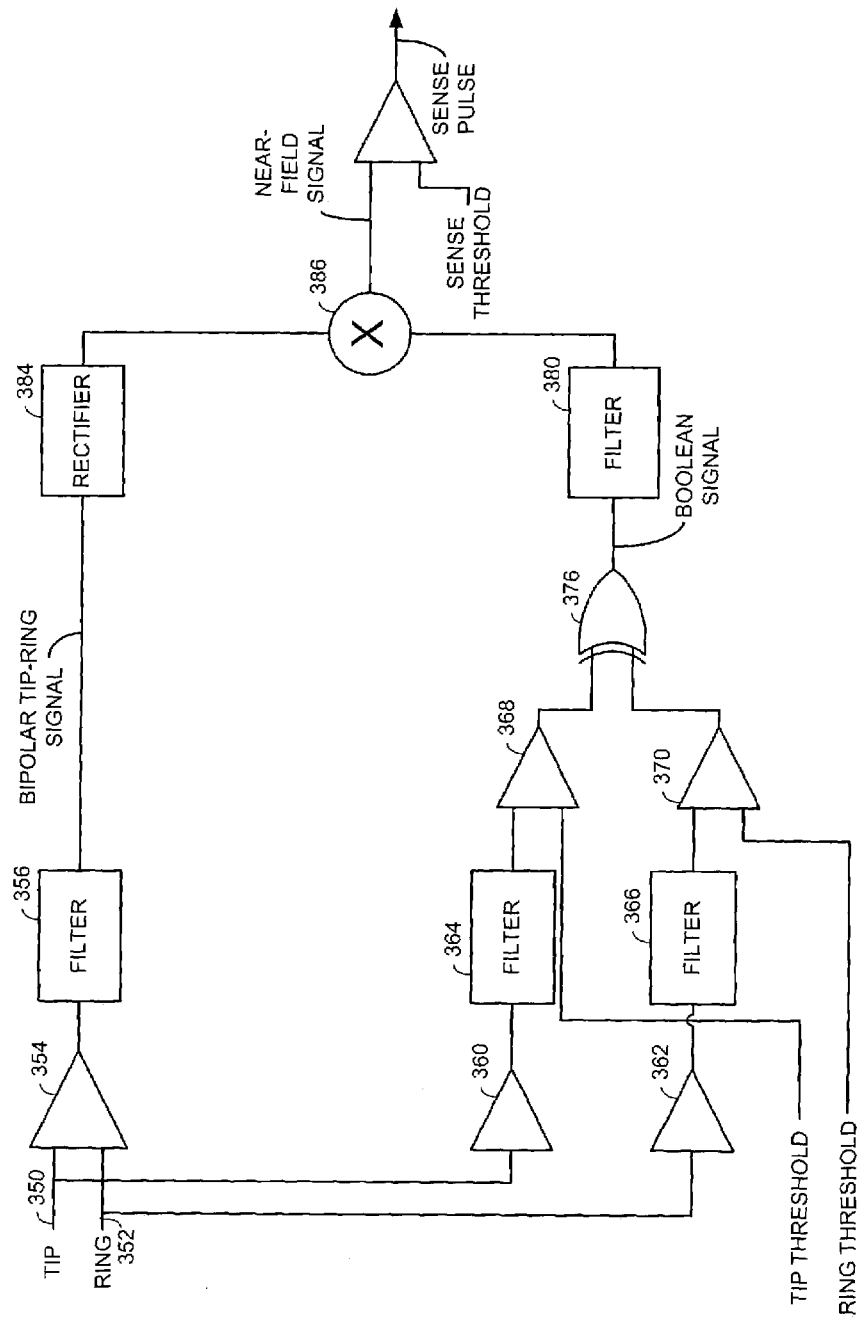
FIG. 10 is a block diagram illustrating components of a second exemplary embodiment of the improved atrial sense amplifier of FIG. 5, which employs a XOR-gate.

Alternatively, a XOR-gate, shown in FIG. 10, is used to generate a true Boolean difference between the two signals. By using a XOR-gate, relative overall strengths of the tip and ring signals during the P-wave are less significant. The implementation of FIG. 10 is similar to that of FIG. 8 and so only pertinent differences will be described in detail. As before, algebraic differences between input unipolar tip and ring signals received on lines 350 and 352 are amplified (by differential amplifier 354) then smoothed (by filter 356) to yield an analog bipolar tip-ring signal. The tip and ring signals are also individually amplified (by amplifiers 360 and 362) then smoothed (by filters 364 and 366.) Although not shown, amplifiers 360 and 362 may also be connected to a unipolar reference signal. Unlike the implementation of FIG. 8, the tip and ring signals are not rectified. Rather, the unrectified tip signal is compared (using bidirectional comparator 368) against a tip threshold, which may be positive or negative, to yield a Boolean tip signal. The bidirectional comparator generates a HIGH output whenever the input signal is either greater than the positive of the threshold or less than the negative of the threshold. The bidirectional comparator generates a LOW output signal otherwise (i.e. whenever the input signal is between the positive and negative values of the threshold.) Likewise, the unrectified ring signal is compared (using bidirectional comparator 370) against a ring threshold, which also may be positive or negative, to yield Boolean ring signal. The Boolean tip and ring signals are then combined using XOR-gate 376. Since a XOR-gate is used, the resulting Boolean difference signal is HIGH whenever the Boolean tip and ring signals are opposite one another and LOW at all other times. The difference signal is smoothed (by filtered 380) then merged (using multiplier 386) with the analog bipolar tip-ring signal (as rectified by rectifier 384) to yield the analog near-field signal. The analog near-field signal is compared against a sense threshold (via comparator 390) to yield the final binary sense pulse signal. Routine experimentation is employed to determine appropriate threshold voltages.

Thus various techniques have been set forth for exploiting near-field propagation delays to filter out far-field signals from electrodes. Although described primarily with respect to the filtering of far-field ventricular events from signals sensed in the atrial, aspects of the invention could potentially also be exploited to filter far-field atrial events from near-field ventricular signals. As can be appreciated, a wide variety of embodiments can be implemented consistent with the principles the invention and no attempt is made herein to describe all possible techniques. In addition, although described primarily with reference to an example wherein the implanted device is a defibrillation/pacer, principles of the invention are applicable to other implantable cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device, a method for rejecting far-field signals, the method comprising:
   defining at least two sensing configurations using a plurality of electrodes in electrical contact with a same chamber of a heart;
   simultaneously sensing a cardiac electrical event using the at least two sensing configurations to generate a pair of sensed signals;
   detecting a timing difference, if any, between the pair of sensed signals;
   rejecting the pair of sensed signals as corresponding to a far-field event if the detected timing difference is less than a selected value; and
   accepting the pair of sensed signals as corresponding to a near-field event if the detected timing difference is greater than the selected value.

2. The method of claim 1 wherein the plurality of electrodes are mounted in the atria and wherein rejecting the sensed signals is performed to ignore signals arising from the ventricles.

3. The method of claim 1 wherein sensing the cardiac electrical event is performed to sense unipolar tip and ring signals and wherein detecting timing differences comprises:
   routing the unipolar tip and ring signals through separate comparators to yield Boolean tip and ring signals; and
   applying the Boolean tip and ring signals to a Boolean logic circuit operative to generate a Boolean difference signal representative of portions of the signal having near-field time delays.

4. The method of claim 3 wherein the Boolean logic circuit includes a XOR-gate and wherein applying the Boolean tip and ring signals to the Boolean logic circuit generates a difference signal having a first value whenever the Boolean tip and ring signals are the same and a having second value whenever the Boolean tip and ring signals are different.

5. The method of claim 3 wherein the Boolean logic circuit includes an AND-gate having a single inverted input and wherein applying the Boolean tip and ring signals to the Boolean logic circuit generates a difference signal having a first value whenever the Boolean Up signal is HIGH and the Boolean ring signal is LOW and having a second value at all other times.

6. The method of claim 3 wherein filtering far-field signals from the pair of sensed signals based on the detected timing difference comprises:
   band-pass filtering the Boolean difference signal;
   combining the analog tip and ring signals to yield a bipolar tip-ring analog signal; and
   combining the filtered output Boolean signal and the bipolar analog tip-ring signal to yield an analog near-field signal representative of substantially only near-field signals.

7. An implantable cardiac stimulation device for rejecting far-field signals, the device comprising:
   at least two electrodes configured for placement in electrical contact with a same chamber of a heart;
   circuitry that is operative to define at least two sensing configurations using the at least two electrodes, wherein the at least two sensing configurations are operative to simultaneously sense a cardiac electrical event and to generate respective pair of sensed signals; and
   a controller connected to the circuitry and operative to receive the respective pair of sensed signals from the at least two sensing configurations, wherein the controller is operative to detect a timing difference, if any, between the sensed signals, and to classify the respective pair of sensed signals as a far-field signal if the detected timing difference is less than a selected value and to classify the respective pair of sensed signals as a near-field signal if the detected timing different is greater than the selected value.

8. The device of claim 7 wherein the electrodes are configured for placement in an atrium and wherein the controller is operative to reject sensed signals arising from the ventricles.

9. A system for use with an implantable cardiac stimulation device for filtering far-field signals, the system comprising:
   means for defining at least two sensing configurations using a plurality of electrodes adapted to be in electrical contact with a same chamber of a heart;
   means for simultaneously sensing a cardiac electrical event using the at least two sensing configurations to generate a pair of sensed signals;

means for detecting a timing difference, if any, between the pair of sensed signals;

means for classifying the cardiac electrical event as a far-field signal if the timing difference is less than a selected value; and means for classifying the cardiac electrical event as a near-field signal if the timing difference is greater than the selected value.

10. The method of claim 1 wherein the selected value is about a few milliseconds.

11. The device of claim 7 wherein the selected value is about a few milliseconds.

12. The system of claim 9 wherein the selected value is about a few milliseconds.

* * * * *